US009382225B2

(12) United States Patent
Samec et al.

(10) Patent No.: US 9,382,225 B2
(45) Date of Patent: Jul. 5, 2016

(54) REDUCTION OF C—O BONDS BY CATALYTIC TRANSFER HYDROGENOLYSIS

(75) Inventors: Joseph Samec, Spånga (SE); Anna Lundstedt, Uppsala (SE); Supaporn Sawadjoon, Uppsala (SE)

(73) Assignee: Kat2Biz AB, Stockholm (SE)

( * ) Notice: Subject to any disclaimer, the term of this patent is extended or adjusted under 35 U.S.C. 154(b) by 0 days.

(21) Appl. No.: 14/003,971

(22) PCT Filed: Mar. 8, 2012

(86) PCT No.: PCT/SE2012/050262
§ 371 (c)(1),
(2), (4) Date: Sep. 9, 2013

(87) PCT Pub. No.: WO2012/121659
PCT Pub. Date: Sep. 13, 2012

(65) Prior Publication Data
US 2013/0345445 A1    Dec. 26, 2013

(30) Foreign Application Priority Data

Mar. 8, 2011 (SE) ..................................... 1150204

(51) Int. Cl.
| | | |
|---|---|---|
| C07D 317/46 | (2006.01) | |
| C07C 1/22 | (2006.01) | |
| C07C 41/18 | (2006.01) | |
| C07C 67/00 | (2006.01) | |
| C07C 29/132 | (2006.01) | |
| C07C 45/61 | (2006.01) | |
| C07B 31/00 | (2006.01) | |
| C07C 1/207 | (2006.01) | |
| C07C 1/32 | (2006.01) | |
| C07C 5/03 | (2006.01) | |
| C07C 29/60 | (2006.01) | |
| C07C 67/31 | (2006.01) | |
| C07C 37/055 | (2006.01) | |
| C07C 45/65 | (2006.01) | |

(52) U.S. Cl.
CPC .............. *C07D 317/46* (2013.01); *C07B 31/00* (2013.01); *C07C 1/2076* (2013.01); *C07C 1/22* (2013.01); *C07C 1/321* (2013.01); *C07C 5/03* (2013.01); *C07C 29/132* (2013.01); *C07C 29/60* (2013.01); *C07C 37/055* (2013.01); *C07C 41/18* (2013.01); *C07C 45/61* (2013.01); *C07C 45/65* (2013.01); *C07C 67/00* (2013.01); *C07C 67/31* (2013.01); *C07C 2523/44* (2013.01)

(58) Field of Classification Search
USPC .................. 549/462; 568/814, 315, 433, 799; 560/75; 585/469
See application file for complete search history.

(56) References Cited

U.S. PATENT DOCUMENTS

| | | | |
|---|---|---|---|
| 4,374,144 | A | 2/1983 | Corbett |
| 4,795,748 | A | 1/1989 | Ross et al. |
| 5,225,591 | A | 7/1993 | Sweeny et al. |
| 6,624,112 | B2 | 9/2003 | Hasegawa et al. |
| 2011/0092707 | A1 | 4/2011 | Burnier |

FOREIGN PATENT DOCUMENTS

| | | |
|---|---|---|
| AU | 699753 B2 | 12/1998 |
| EP | 0008885 A1 | 3/1980 |
| EP | 0013067 A1 | 7/1980 |
| EP | 0170028 A1 | 2/1986 |
| EP | 1238700 A1 | 9/2002 |
| GB | 2197865 A | 6/1988 |
| JP | S5538371 A | 3/1980 |
| JP | S5587794 A | 7/1980 |
| JP | S6118760 A | 1/1986 |
| JP | H09-509946 A | 10/1997 |
| JP | 2002-263490 A | 9/2002 |
| WO | WO-95/23779 A2 | 9/1995 |

OTHER PUBLICATIONS

Supplementary European Search Report dated Aug. 18, 2014 issued in corresponding European Application No. 12754925.1.
Prasad, Kapa et al. "New Trends in Palladium-Catalyzed Transfer Hydrogenations Using Formic Acid." *Advanced Synthesis & Catalysis*, vol. 347, No. 14 (2005): 1769-1773.
Sawadjoon, Supaporn et al. "Pd-Catalyzed Transfer Hydrogenolysis of Primary, Secondary, and Tertiary Benzylic Alcohols by Formic Acid: A Mechanistic Study." *American Chemical Society*, vol. 3, No. 4 (2013): 635-642.
Vatèle, Jean-Michel and Stephen Hanessian. "Design and Reactivity of Organic Functional Groups—Preparation and Nucleophilic Displacement Reactions of Imidazole-1-sulfonates (Imidazylates)." *Tetrahedron*, vol. 52, No. 32 (1996): 10557-10568.
Kieboom, A.P.G. et al. "Substituent Effects in the Hydrogenolysis of Benzyl Alcohol Derivatives Over Palladium." *Journal of Catalysis*, vol. 20 (1971): 58-66.
Ranade, Vidyadhar S. and Roel Prins. "Hydrogenolysis of Benzylic Alcohols on Rhodium Catalysts." *Chemistry—A European Journal*, vol. 6, No. 2 (2000): 313-320.
Huber, George W. et al. "Renewable Alkanes by Aqueous-Phase Reforming of Biomass-Derived Oxygenates." *Angewandte Chemie International Edition*, vol. 43 (2004): 1549-1551.
Huber, George W. and James A Dumesic. "An overview of aqueous-phase catalytic processes for production of hydrogen and alkanes in a biorefinery." *Catalysis Today*, vol. 111 (2006): 119-132.
Simonetti, Dante A. and James A. Dumesic. "Catalytic Production of Liquid Fuels from Biomass-Derived Oxygenated Hydrocarbons: Catalytic Coupling at Multiple Length Scales." *Catalysis Reviews*, vol. 51 (2009): 441-484.
Chheda, Juben N. et al. "Liquid-Phase Catalytic Processing of Biomass-Derived Oxygenated Hydrocarbons to Fuels and Chemicals." *Angewandte Chemie International Edition*, vol. 46 (20007): 7164-7183.

(Continued)

*Primary Examiner* — Kristin Vajda
(74) *Attorney, Agent, or Firm* — Harness, Dickey & Pierce, P.L.C.

(57) ABSTRACT

The present invention relates to a method of reducing a C—O bond to the corresponding C—H bond in a substrate which could be a benzylic alcohol, allylic alcohol, ester, or ether or an ether bond beta to a hydroxyl group or alpha to a carbonyl group.

16 Claims, 3 Drawing Sheets

(56) References Cited

OTHER PUBLICATIONS

Feng, Jian et al. "Catalytic transfer hydrogenolysis of α-methylbenzyl alcohol using palladium catalysts and formic acid." *Applied Catalysis A: General*, vol. 354 (2009): 38-43.

Liu, X. et al. "Catalytic transfer hydrogenolysis of 2-phenyl-2-propanol over palladium supported on activated carbon". Elsevier B.V., Journal of Molecular Catalysis A: Chemical 252, p. 176-180; 2006.

Feng, J. et al. "Catalytic transfer hydrogenolysis of a-rnethylbenzyl alcohol using palladium catalysts and formic acid". Elsevier B.V., Applied Catalysis A: General 354, p. 38-43; 2008.

Rajagopal, S. et al. "Palladium-catalyzed transfer hydrogenolysis of benzyl acetate with ammonium formate". Elsevier B.V., Applied Catalysis A: General 152, p. 69-81; 1997.

International Search Report PCT/ISA/210 for PCT/SE2012/050262 dated May 11, 2012.

Xikang LV, et al., *The Effect on Glycerol Hydrogenolysis Reaction Catalyzed by Pt/TiO$_2$*, Proceedings of the 6th National Conference on Environmental Catalysts and Materials of China, pp. 336-337 (Dec. 31, 2009).

Ley, et al., "Recyclable Polyurea-Microencapsulated Pd(0) Nanoparticles: An Efficient Catalyst for Hydrogenolysis of Epoxides," *Organic Letters*, vol. 5, No. 24, Sep. 24, 2003, pp. 4665-4668.

Hattori, et al., "Chemoselective Control of Hydrogenation Among Aromatic Carbonyl and Benzyl Alcohol Derivatives Using Pd/C(en) Catalyst," *Tetrahedron*, vol. 57, Apr. 10, 2011, pp. 4817-4824.

REDUCTION OF C—O BONDS BY CATALYTIC TRANSFER HYDROGENOLYSIS

This application is the national phase under 35 U.S.C. §371 of PCT International Application No. PCT/SE2012/050262 which has an International filing date of Mar. 8, 2012, which claims priority to Swedish patent application number SE 1150204-4 filed Mar. 8, 2011.

TECHNICAL FIELD

The present invention relates to a methodology to reduce benzylic alcohols, esters, ethers, and olefins to the corresponding hydrocarbon.

BACKGROUND

Reduction of alcohols to the corresponding hydrocarbon is usually accomplished in two consecutive steps. First, the hydroxyl is reacted to generate a sulfonate, halide or epoxide, and then these derivatives are reacted with a reducing agent (S. Hanessian, 1996). Alternative strategies include Barton-MacCombie radical reduction of a sulfur manipulated hydroxyl group (S. Z. Zard, 1997). By oxidizing the alcohol to a ketone the Wolf-Kischner or Clemmensen reductions generate the corresponding hydrocarbons (D. Todd, 1948, E. L. Martin, 1942). All these methodologies suffer from being two step processes and the fact that stoichiometric amount of reagents are used.

The formal catalytic reduction of alcohols to their corresponding alkanes is a rare transformation in organic chemistry. Most studies have used transition metals based on palladium (H. van Bekkum, 1971, 2007), but also ruthenium (M. Schlaf, 2009), and rhodium (R. Prins, 2000) have been reported. Traditionally, hydrogen gas has been employed in catalytic hydrogenolysis to generate the alkane and water as side product.

The formal reduction of alcohols to the corresponding hydrocarbon can also be accomplished by elimination-reduction methodology (G. W. Huber, 2004, J. A. Dumesic, 2006, 2007, 2008, 2009) at high reaction temperatures and pressure.

More recently, formic acid has been employed as the source of hydrogen and the reaction is termed catalytic transfer hydrogenolysis (H. Chen, 2009, G. Lu, 2006). The use of formic acid as hydrogen source has many advantages in regards to handling, transport, and storage and can easily be generated from hydrogen gas and carbon dioxide (P. G. Jessop, 2004). Furthermore, formic acid is not explosive and is not hazardous compared to methanol. Because the generated carbon dioxide can be recycled into formic acid with the addition of hydrogen gas, the reaction is atom efficient where only water is formed as side-product in the net reaction. A problem with the reported procedures in which formic acid has been used as the reductant in the transfer hydrogenolysis of alcohols, is a competing disproportionation reaction that limits the efficiency of the process. In fact we have found that the reported transfer hydrogenolysis reported actually is a tandem disproportionation and transfer hydrogenation process in which the formed ketone from the disproportionation is continuously reduced by transfer hydrogenation to regenerate the alcohol. That is, the alcohol is favored as hydrogen donor over the formic acid. That is, the reaction to generate 50% hydrocarbon is fast, followed by a slower process where the formic acid reduces the ketone to the alcohol in a transfer hydrogenation followed by a transfer hydrogenolysis (FIG. 1).

SUMMARY

The object of the present invention is to provide a way to perform a transfer hydrogenolysis of primary, secondary, and tertiary alcohols where the competing disproportionation is inhibited. This has to the knowledge of the present inventors never before been presented.

The invention can, but is not limited to, be used in any application regarding reduction of benzylic or allylic alcohols, esters, carbonyls or ethers and also the reduction and depolymerization of a material consisting of benzylic or allylic alcohols, esters, carbonyls or ethers. The invention can be used in a wide variety of applications ranging from the depolymerization of lignin to generate hydrocarbon monomers that can be used as fine chemical feed-stock or fuel additives to processes to deoxygenate the said functional groups in the synthesis of any chemical compound including, but not limited to, precursors to or: active pharmaceutical ingredients, fragrances, or plasticizer.

One aspect of the present invention relates to a method of reducing a C—O bond to the corresponding C—H bond in a substrate using a hydrogen donor, a metal catalyst and a base in a solvent mixture comprising at least two solvents wherein one is water.

Another aspect relates to a method of reducing a C—O bond to the corresponding C—H bond in a substrate using a hydrogen donor, a metal catalyst in a solvent mixture comprising at least two solvents, wherein one is water, and an atmosphere comprising carbon dioxide.

Preferred embodiments of the above mentioned aspects are described below, all the embodiments below should be understood to refer to both aspects described above.

In one embodiment the hydrogen donor is formic acid or hydrogen gas.

In another embodiment one solvent is a polar, unpolar, protic or aprotic solvent.

In another embodiment one solvent is selected between methanol, ethanol, benzene, THF or toluene.

In another embodiment the solvent mixture comprises ethanol and water.

In another embodiment the solvent mixture comprises methanol and water.

In another embodiment the solvent mixture comprises benzene and water.

In another embodiment the base is an inorganic base or an organic base.

In another embodiment the hydrogen donor is formic acid or hydrogen gas.

In another embodiment the hydrogen donor is not hydrogen gas.

In another embodiment the amount of base is not stoichiometric to the amount of the substrate.

In another embodiment the amount of base is not stoichiometric to the amount of the substrate unless the substrate is an ether either situated in alpha position to a carbonyl or in beta position to an alcohol.

In another embodiment the reaction is conducted at a temperature of at least 40° C., preferably 70-100° C.

In another embodiment the catalyst is a transition metal catalyst, preferably based on palladium.

In another embodiment the substrate is a benzylic alcohol, ester, or ether.

In another embodiment the benzylic alcohol is either a primary, secondary or tertiary alcohol.

In another embodiment the phenyl group of the benzylic alcohol is substituted in either ortho, meta or para position.

In another embodiment the substrate is an olefin.

In another embodiment the substrate is a polymer.

In another embodiment the substrate is a biopolymer.

In another embodiment the substrate is lignin.

In another embodiment the substrate is lignosulfonate.

In another embodiment the reaction is conducted in an over pressure of carbon dioxide.

In another embodiment the reaction is conducted using palladium on charcoal.

The present invention could be used to depolymerize a material based on benzylic alcohol, ether, and ester function/functions in large molecules.

The present invention could be used to depolymerize a material based on benzylic alcohol, ether, olefin, and ester function/functions in lignin.

The present invention could be used to reduce graphene oxide to graphene.

The present invention could be used to depolymerize and reduce a di- or polymer of a carbohydrate.

The present invention could be used to reduce benzylic alcohols to yield the corresponding hydrocarbon in good to excellent yield.

In another embodiment the solvent mixture consisting of any solvent (protic, aprotic, polar or non-polar) and water in a 1:1 to 10:1 ratio is used.

In another embodiment the catalyst is used in 0.1-10 mol %.

In another embodiment the formic acid is used in 1-5 equivalents to alcohol.

In another embodiment palladium on charcoal is exposed to a base (organic, inorganic, strong or weak) prior to reaction with substrate.

In another embodiment hydrogen gas is used alone or in combination with formic acid in the hydrogenolysis of benzylic alcohols.

DETAILED DESCRIPTION

Figure 1:
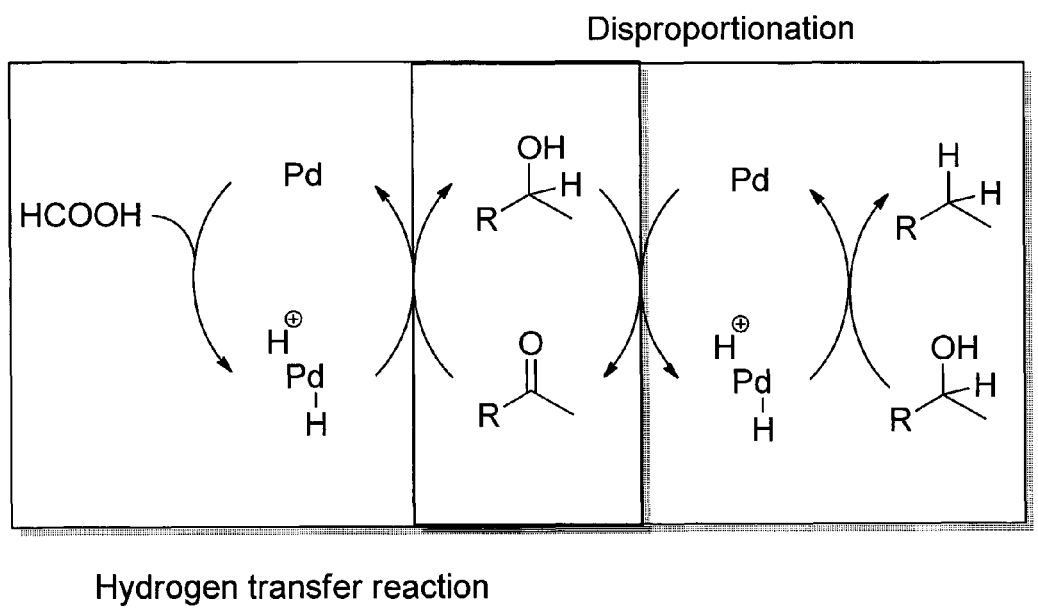
FIG. 1. The method according to the present invention. The transfer hydrogenolysis of 1-phenylethanol can be seen as a tandem hydrogen transfer process in which the catalyst dehydrogenates the alcohol to the corresponding ketone. By this process, the reaction proceeds to 50% conversion in a fast step. After this initial disproportionation a hydrogen transfer process takes place to regenerate the alcohol from the ketone and formic acid.

In the present invention the term "hydrogen donor" should be interpreted as a substance or compound that gives or transfers a hydrogen atom to another substance or compound.

The invention relates to a method to reduce a substrate wherein said substrate can be but is not limited to primary, secondary and tertiary benzylic or allylic alcohol, benzylic or allylic ether, benzylic or allylic carbonyl, and benzylic or allylic ester, or olefins to the corresponding hydrocarbon. Preferably, the substrate is a secondary or tertiary alcohol except for allylic alcohols than primary are more preferred.

A general method comprises adding a catalyst to a reaction flask or container. Adding a solvent mixture of at least two solvents where one of the solvents is water and a base. The mixture is then heated followed by addition of a hydrogen donor and the substrate to be reduced. The reaction is then stopped or quenched and the obtained product is isolated and preferably dried.

The phenyl group may be substituted in ortho, meta or para position. The reaction is performed using a transition metal catalyst (Pd, Pt, Rh e.g. Pd/C or Rh/C) to generate the hydrocarbon in good (45-65% yield) to excellent yields (65-100% yield) with only water as side product. The yield of the reduced product according to the invention is often more than 90% and often 100%. The amount of catalyst can be 0.5 to 20 mol %, such as 0.5 mol % or more, or 1 mol % or more, or 2 mol % or more, or 4 mol % or more, or 5 mol % or more, or 8 mol % or more, or 20 mol % or less, or 15 mol % or less or 12 mol % or less or 10 mol % or less.

The reactions can be performed under mild reaction conditions (40° C.-100° C.) by conventional heating or by heating in a microwave oven, but can also be performed at higher reaction temperatures. The reactions are performed in a solvent mixture comprising at least two solvents. One of these solvents can be any solvent (for example: ethanol, methanol, propanol, benzene, THF, toluene, DMF, DMSO, ethyl acetate) and the other solvent is water, preferably in a ratio of 1-10:1 for example 1:1, 2:1, 3:1, 4:1, 5:1, 6:1, 7:1, 8:1, 9:1 or 10:1. The range could be 1:1 or more, or 2:1 or more or 3:1 or more, or 4:1 or more, or 10:1 or less, or 9:1 or less, or 8:1 or less, or 7:1 or less, or 6:1 or less. A preferred range is 2:1 to 6:1, or 3:1 to 5:1.

In order to inhibit the disproportionation, a base or carbon dioxide should be added to the solvent mixture and catalyst prior to addition of a hydrogen donor such as formic acid or hydrogen gas and substrate (vide infra for mechanistic discussion concerning the base). The amount of hydrogen donor such as formic acid could be between 1 to 5 equivalents such as 1, 2, 3, 4 and 5 equivalents. In one embodiment the amount of hydrogen donor is 1.5 to 4.5 equivalents, and in another embodiment the amount of hydrogen donor is 2 to 4 equivalents, and in yet another embodiment the amount of hydrogen donor is 2.5 to 3.5 equivalents. In one embodiment the hydrogen donor is not hydrogen gas.

Figure 2:
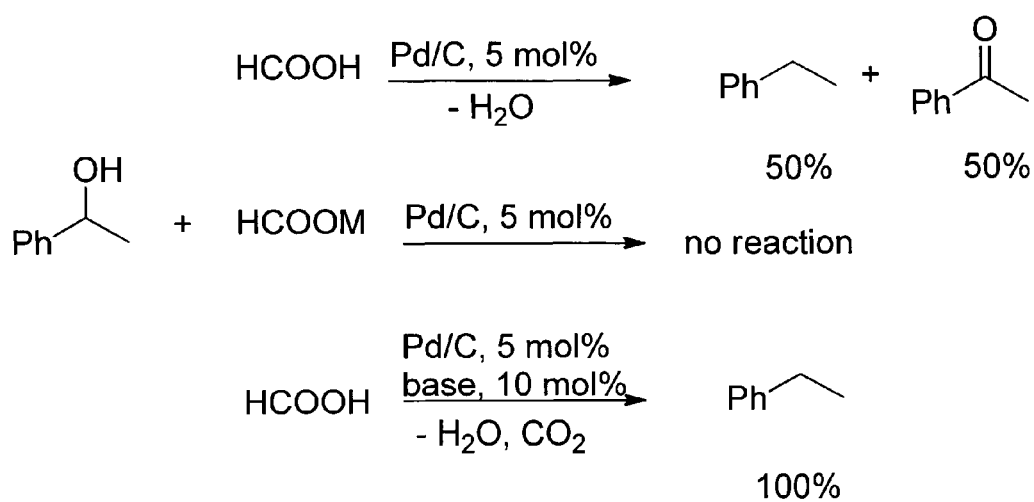
FIG. 2. Apparent transfer hydrogenolysis is actually a disproportionation in which 1 equivalent of alcohol generate 0.5 equivalent of hydrocarbon and 0.5 equivalent of ketone. With stoichiometric amount of base neither disproportionation nor transfer hydrogenolysis occurs. Using catalytic amount of base generates an efficient transfer hydrogenolysis in which less than 15% of ketone is observed during the reaction.

Any base could be used and could be selected from but not limited to ammonium formate, sodium bicarbonate and triethylamine. Any amount of base or carbon dioxide pressure can be used. Preferably in an amount of 5 mol % or more of base added, or more than 10 mol %, or more than 20 mol % but not more than 50 mol %, or less than 40 mol % or less than 30 mol %. However, stoichiometric amount of base (to the substrate) inhibits all reactivity (FIG. 2), unless when the substrate is an ether either situated in alpha position to a carbonyl or in beta position to an alcohol, then a stoichiometric amount of base is required for the cleavage of the ether bond. In the latter case when the substrate is an ether, the substrate can be either a benzylic-substrate or an allylic-substrate, preferably an allylic-substrate.

It should be noted that a disproportionation is feasible in the absence (and also presence) of formic acid to generate 50% conversion of the hydrocarbon. In the presence of base this disproportionation is inhibited and only starting material is recovered if an alcohol is used as substrate and no formic acid is added. If formic acid is added to the reaction mixture including a base, a facile transfer hydrogenolysis is obtained where the corresponding hydrocarbon is obtained in 65-100% yield. The solvent mixture is heated preferably to a temperature between 40 and 100° C., depending on the solvent, more preferably 70-100° C., more preferably 75 to 90° C., such as 75° C., 80° C., 85° C. or 90° C.

When using a carbon dioxide atmosphere, the atmosphere may comprise other compounds such as oxygen and nitrogen. The atmosphere could be air comprising carbon dioxide or an inert atmosphere (such as argon or nitrogen gas) comprising carbon dioxide.

Figure 3:
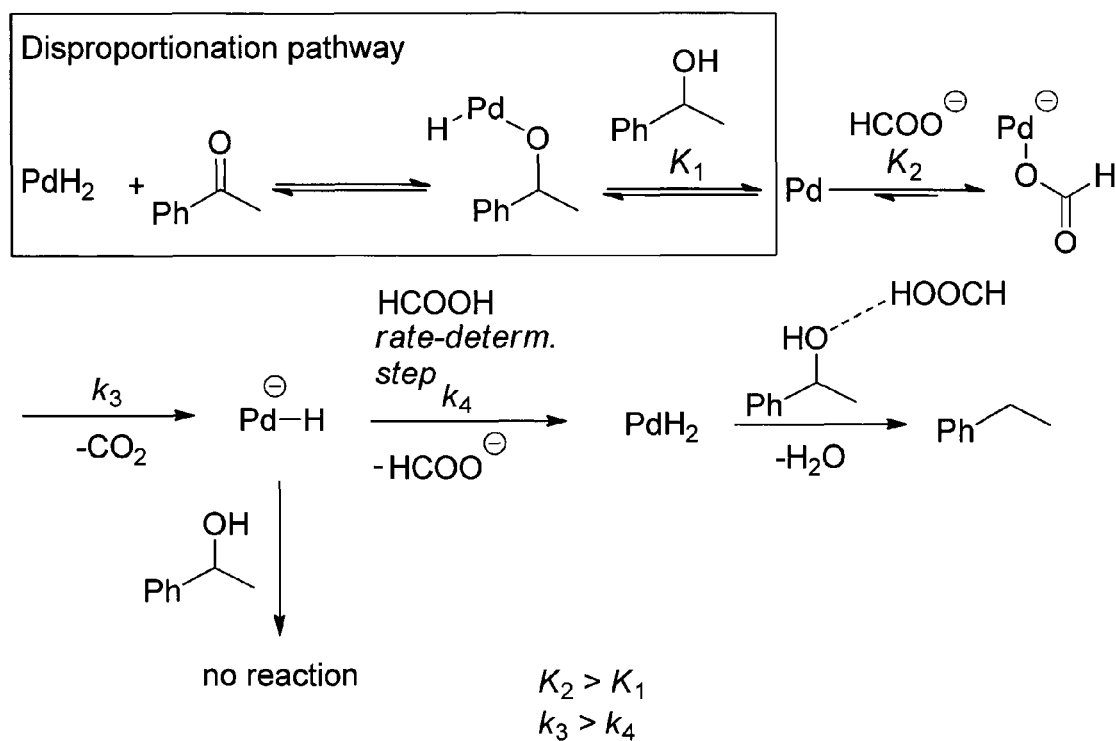
FIG. 3. Because the negative charge of the base, the formate competes for the vacant coordination site of palladium thus inhibiting the disproportionation pathway in which an alcohol would coordinate. With equimolar amount of base, no reactivity is observed for alcohols in contrast to halides and esters, because of the poor leaving group ability of the hydroxyl group.
Figure 4:
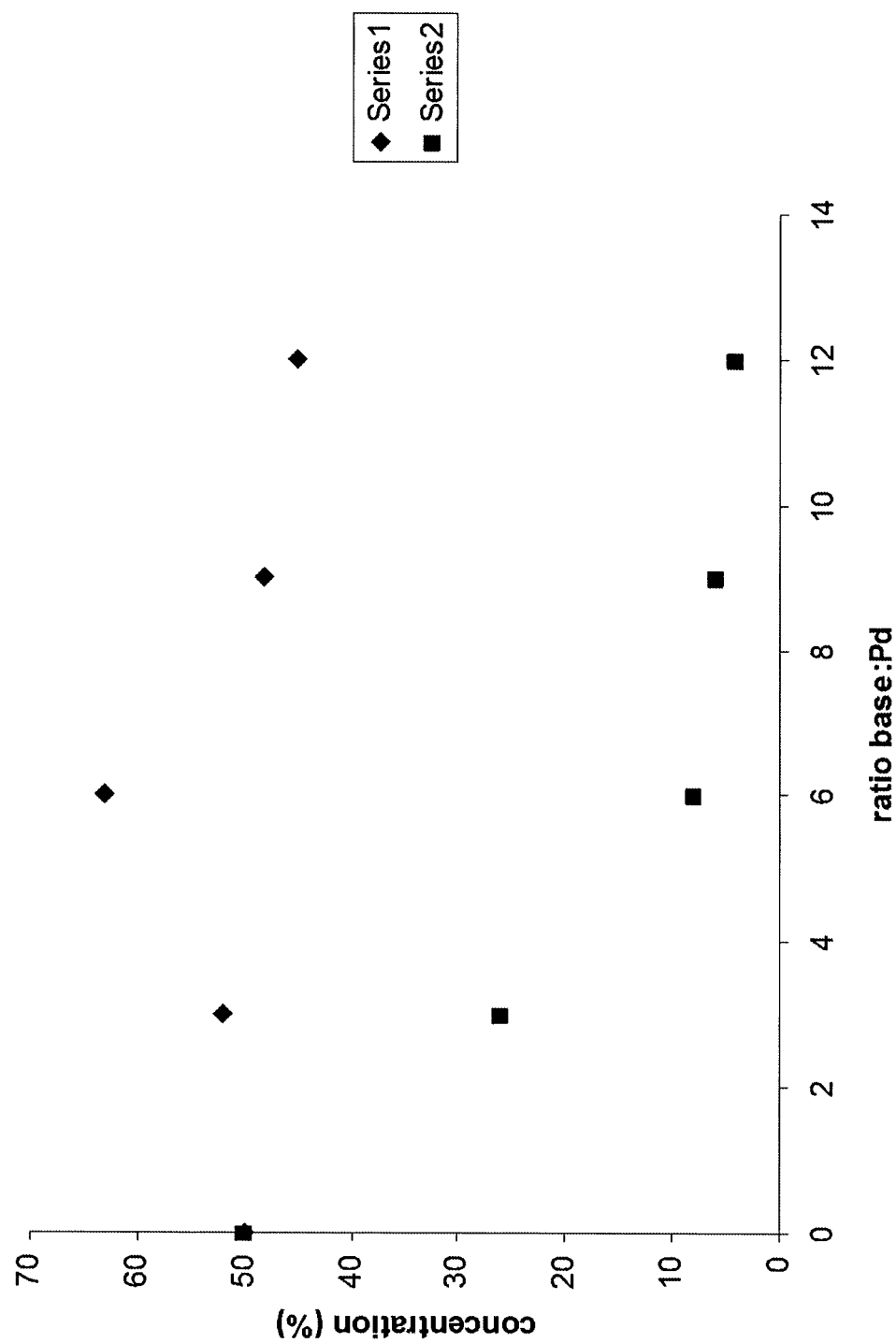
FIG. 4. Series 1 correspond to ethylbenzene and Series 2 correspond to acetophenone.

The formate ion (or other base) may coordinate to palladium. This coordination inhibits a ligand exchange by the benzylic alcohol and thereby also the disproportionation pathway (FIG. 3, $K_2 > K_1$). Because the disproportionation is not completely inhibited unless stoichiometric amounts of base is used we believe that the [Pd—OCHO]$^-$ complex does not decompose into Pd—H$^-$ complex directly, although not rate-limiting (since $k_{HCOOH}/k_{DCOOH} = 1.07$). The Pd—H$^-$ cannot promote transfer hydrogenolysis in the absence of activation by acid because this would require the hydroxyl group to be the leaving group. A proton from the formic acid generates a neutral PdH$_2$ species in a rate limiting step ($k_3 > k_4$). This would explain the deuterium isotope effect of formic acid ($k_{HCOOH}/k_{HCOOD} = 2.66$). Alternatively, the formic acid protonates the hydroxyl group of the benzylic alcohol. Probably, a combination of both protonations is operating. The fact that the Pd-catalyzed disproportionation alone is facilitated by formic acid supports this. Noteworthy, transfer hydrogenolysis of both benzylic esters and halides are promoted using formate salts. The greater leaving group ability for these substrates would not require prior protonation as in the case of benzylic alcohols.

The following substrates are non-limiting examples of substrates that could be reduced by the method according to the invention 1-phenylethanol, 2-Phenyl-2-propan-2-ol, benzyl alcohol, 1-methoxy-1-phenylethane, 1-(phenylethyl) formate, styrene, 4-Phenyl-3-butene-2-ol, phenylmethanesulfonic acid, 3-(4-(2-(4-hydroxy-3-methoxyphenyl)-2-oxoethoxy)phenyl)acrylaldehyde, ethyl 3-(4-(2-(4-hydroxy-3-methoxyphenyl)-2-oxoethoxy)phenyl)acrylate, 2-phenoxy-1-phenylethanone and 1,4-bis(benzo[d][1,3]dioxol-5-yl)hexahydrofuro[3,4-c]furan.

EXAMPLES

Example 1

Transfer Hydrogenolysis of 1-Phenylethanol

Pd/C (5 mol %, 42 mg, 0.021 mmol) is weighed into a reaction flask. A solvent mixture consisting of ethanol (2.4 mL) and water (0.6 mL) and ammonium formate (6 mg, 0.095 mmol, 30 mol %) is added, the reaction flask is capped with a rubber septa and the mixture is heated (80° C.) for 2 minutes. Formic acid (50 µL, 1.05 mmol, 3 equivalents) and then 1-phenylethanol (50 µL, 0.42 mmol) are added by syringe. The reaction is run for 10-40 minutes and the reaction is quenched with brine. The product is extracted by DCM and the organic phase is dried by Na$_2$SO$_4$. The product ethylbenzene was analyzed by $^1$H NMR and produced in 100% yield.

Example 2

Transfer Hydrogenolysis of 1-Phenylethanol

Pd/C (5 mol %) is weighed into a reaction flask. A solvent mixture consisting of benzene and water (4:1) and ammonium formate (30 mol %) is added, the reaction flask is capped with a rubber septa and the mixture is heated (80° C.) for 2 minutes. Formic acid (3 equivalents) and then 1-phenylethanol are added by syringe. The reaction is run for 10-40 minutes and the reaction is quenched with brine. The product is extracted by DCM and the organic phase is dried by Na$_2$SO$_4$. The product ethylbenzene was analyzed by $^1$H NMR and produced in 100% yield.

Example 3

Transfer Hydrogenolysis of 1-Phenylethanol

Pd/C (5 mol %) is weighed into a reaction flask. A solvent mixture consisting of ethanol and water (4:1) and sodium bicarbonate (30 mol %) is added, the reaction flask is capped with a rubber septa and the mixture is heated (80° C.) for 2 minutes. Formic acid (3 equivalents) and then 1-phenylethanol are added by syringe. The reaction is run for 10-40 minutes and the reaction is quenched with brine. The product is extracted by DCM and the organic phase is dried by Na$_2$SO$_4$. The product ethylbenzene was analyzed by $^1$H NMR and produced in 100% yield.

Example 4

Transfer Hydrogenolysis of 1-Phenylethanol

Pd/C (5 mol %) is weighed into a reaction flask. A solvent mixture consisting of ethanol and water (4:1), the reaction flask is capped with a rubber septa and an atmosphere of carbon dioxide is applied. The reaction flask is heated (80° C.) for 2 minutes. Formic acid (3 equivalents) and then 1-phenylethanol are added by syringe. The reaction is run for 10-40 minutes and the reaction is quenched with brine. The product is extracted by DCM and the organic phase is dried by Na$_2$SO$_4$. The product ethylbenzene was analyzed by $^1$H NMR and produced in 100% yield.

Example 5

Transfer Hydrogenolysis of 2-Phenyl-2-propan-2-ol

Pd/C (5 mol %, 42 mg, 0.021 mmol) is weighed into a reaction flask. A solvent mixture consisting of ethanol (2.4 mL) and water (0.6 mL) and ammonium formate (6 mg, 0.095 mmol, 30 mol %) is added, the reaction flask is capped with a rubber septa and the mixture is heated (80° C.) for 2 minutes. Formic acid (50 µL, 1.05 mmol, 3 equivalents) and then 2-Phenyl-2-propan-2-ol (58 µL, 0.42 mmol) are added by syringe. The reaction is run for 10-40 minutes and the reaction is quenched with brine. The product is extracted by DCM and the organic phase is dried by Na$_2$SO$_4$. The product isopropylbenzene was analyzed by $^1$H NMR and produced in 98% yield.

Example 6

Transfer Hydrogenolysis of Benzyl Alcohol

Pd/C (5 mol %, 42 mg, 0.021 mmol) is weighed into a reaction flask. A solvent mixture consisting of ethanol (2.4 mL) and water (0.6 mL) and ammonium formate (6 mg, 0.095 mmol, 30 mol %) is added, the reaction flask is capped with a rubber septa and the mixture is heated (80° C.) for 2 minutes. Formic acid (50 µL, 1.05 mmol, 3 equivalents) and then benzyl alcohol (43 µL, 0.42 mmol) are added by syringe. The reaction is run for 10-40 minutes and the reaction is quenched with brine. The product is extracted by DCM and the organic phase is dried by $Na_2SO_4$. The product toluene was analyzed by $^1H$ NMR and produced in 70% yield.

Example 7

Transfer Hydrogenolysis of 1-Phenylethane-1,2-diol

Pd/C (5 mol %) is weighed into a reaction flask. A solvent mixture consisting of ethanol and water (4:1) and ammonium formate (30 mol %) is added, the reaction flask is capped with a rubber septa and the mixture is heated (80° C.) for 2 minutes. Formic acid (3 equivalents) and then benzyl alcohol are added by syringe. The reaction is run for 10-40 minutes and the reaction is quenched with brine. The product is extracted by DCM and the organic phase is dried by $Na_2SO_4$. The product 1-phenyl-2-propanol was analyzed by $^1H$ NMR and produced in 60% yield.

Example 8

Transfer Hydrogenolysis of 1-Methoxy-1-phenylethane

Pd/C (5 mol %) is weighed into a reaction flask. A solvent mixture consisting of ethanol and water (4:1) and ammonium formate (30 mol %) is added, the reaction flask is capped with a rubber septa and the mixture is heated (80° C.) for 2 minutes. Formic acid (3 equivalents) and then benzyl alcohol are added by syringe. The reaction is run for 20 minutes and the reaction is quenched with brine. The product is extracted by DCM and the organic phase is dried by $Na_2SO_4$. The product ethylbenzene was analyzed by $^1H$ NMR and produced in 60% yield.

Example 9

Transfer Hydrogenolysis of 1-(Phenylethyl) Formate

Pd/C (5 mol %) is weighed into a reaction flask. A solvent mixture consisting of ethanol and water (4:1) and ammonium formate (30 mol %) is added, the reaction flask is capped with a rubber septa and the mixture is heated (80° C.) for 2 minutes. Formic acid (3 equivalents) and then benzyl alcohol are added by syringe. The reaction is run for 20 minutes and the reaction is quenched with brine. The product is extracted by DCM and the organic phase is dried by $Na_2SO_4$. The product ethylbenzene was analyzed by $^1H$ NMR and produced in 20% yield.

Example 10

Transfer Hydrogenation of Styrene

Pd/C (5 mol %) is weighed into a reaction flask. A solvent mixture consisting of ethanol and water (4:1) and ammonium formate (30 mol %) is added, the reaction flask is capped with a rubber septa and the mixture is heated (80° C.) for 2 minutes. Formic acid (3 equivalents) and then styrene are added by syringe. The reaction is run for 20 minutes and the reaction is quenched with brine. The product is extracted by DCM and the organic phase is dried by $Na_2SO_4$. The product ethylbenzene was analyzed by $^1H$ NMR and produced in 100% yield.

Example 11

Hydrogenolysis of Phenylethanol

Pd/C (5 mol %) is weighed into a reaction flask. A solvent mixture consisting of ethanol and water (4:1) and ammonium formate (30 mol %) is added, the reaction flask is capped with a rubber septa and the mixture is heated (80° C.) for 2 minutes. The solution is bubbled with hydrogen gas for 5 minutes and 1-phenylethanol is added by syringe. The reaction is run for 40 minutes and the reaction is quenched with brine. The product is extracted by DCM and the organic phase is dried by $Na_2SO_4$. The product ethylbenzene was analyzed by $^1H$ NMR and produced in 100% yield.

Example 12

Transfer Hydrogenolysis of Phenylethanol in a Hydrogenolysis Reaction Medium

Pd/C (5 mol %) is weighed into a reaction flask. A solvent mixture consisting of ethanol and water (4:1) and ammonium formate (30 mol %) is added, the reaction flask is capped with a rubber septa and the mixture is heated (80° C.) for 2 minutes. Formic acid (3 equivalents) is added, the solution is bubbled with hydrogen gas for 5 minutes, and then 1-phenylethanol is added by syringe. The reaction is run for 40 minutes and the reaction is quenched with brine. The product is extracted by DCM and the organic phase is dried by $Na_2SO_4$. The product ethylbenzene was analyzed by $^1H$ NMR and produced in 100% yield.

Example 13

Transfer Hydrogenolysis of Phenylethanol

Pd/C (5 mol %) is weighed into a reaction flask. A solvent mixture consisting of ethanol and water (4:1) and $NaHCO_3$ (30 mol %) is added, the reaction flask is capped with a rubber septa and the mixture is heated (80° C.) for 2 minutes. Formic acid (3 equivalents) is added, the solution is bubbled with hydrogen gas for 5 minutes, and then 1-phenylethanol is added by syringe. The reaction is run for 40 minutes and the reaction is quenched with brine. The product is extracted by DCM and the organic phase is dried by $Na_2SO_4$. The product ethylbenzene was analyzed by $^1H$ NMR and produced in 100% yield.

Example 14

Transfer Hydrogenolysis of Phenylethanol

Pd/C (5 mol %) is weighed into a reaction flask. A solvent mixture consisting of ethanol and water (4:1) and triethylamine (30 mol %) is added, the reaction flask is capped with a rubber septa and the mixture is heated (80° C.) for 2 minutes. Formic acid (3 equivalents) is added, the solution is bubbled with hydrogen gas for 5 minutes, and then 1-phenylethanol is added by syringe. The reaction is run for 40 minutes and the reaction is quenched with brine. The product is extracted by DCM and the organic phase is dried by $Na_2SO_4$. The product ethylbenzene was analyzed by $^1H$ NMR and produced in 100% yield.

Example 15

Effect of the Base in the Transfer Hydrogenolysis of Phenylethanol

Pd/C (5 mol %) is weighed into a reaction flask. A solvent mixture consisting of ethanol and water (4:1) and ammonium formate (0-12 equivalents to palladium) is added, the reaction flask is capped with a rubber septa and the mixture is heated (80° C.) for 2 minutes. Formic acid (3 equivalents) is added, the solution is bubbled with hydrogen gas for 5 minutes, and then 1-phenylethanol is added by syringe. The reaction is run for 12 minutes and the reaction is quenched with brine. The product is extracted by DCM and the organic phase is dried by $Na_2SO_4$. The product ethylbenzene and acetophenone was analyzed by $^1H$ NMR compared to an internal standard (See FIG. 1).

Example 16

Transfer Hydrogenolysis of 4-Phenyl-3-butene-2-ol

Pd/C (5 mol %) is weighed into a reaction flask. A solvent mixture consisting of ethanol and water (4:1) and $NaHCO_3$ (30 mol %) is added, the reaction flask is capped with a rubber septa and the mixture is heated (80° C.) for 2 minutes. Formic acid (3 equivalents) is added, the solution is bubbled with hydrogen gas for 5 minutes, and then 4-Phenyl-3-butene-2-ol is added by syringe. The reaction is run for 40 minutes and the reaction is quenched with brine. The product is extracted by DCM and the organic phase is dried by $Na_2SO_4$. The product ethylbenzene was analyzed by $^1H$ NMR and produced in 100% yield.

Example 17

Transfer Hydrogenolysis of Phenylmethanesulfonic Acid

Pd/C (5 mol %) is weighed into a reaction flask. A solvent mixture consisting of ethanol and water (4:1) and ammonium formate (30 mol %) is added, the reaction flask is capped with a rubber septa and the mixture is heated (80° C.) for 2 minutes. Formic acid (3 equivalents) and then phenylmethanesulfonic acid (1 equivalents) are added by syringe. The reaction is run for 10-40 minutes and the reaction is quenched with brine. The product is extracted by DCM and the organic phase is dried by $Na_2SO_4$. The product toluene was analyzed by $^1H$ NMR and produced in 95% yield.

Example 18

Generating Ethylbenzene from 1-Phenylethanol

Rh/C (5 mol %) is weighed into a reaction flask. A solvent mixture consisting of ethanol and water (4:1) and ammonium formate (30 mol %) is added, the reaction flask is capped with a rubber septa and the mixture is heated (80° C.) for 2 minutes. Formic acid (3 equivalents) and then 1-phenylethanol are added by syringe. The reaction is run for 4 h and the reaction is quenched with brine. The product is extracted by DCM and the organic phase is dried by $Na_2SO_4$. The product ethylbenzene was analyzed by $^1H$ NMR and produced in 50% yield.

Example 19

Generating 1-(4-Hydroxy-3-methoxyphenyl)ethanone and 3-(4-Hydroxyphenyl)acrylaldehyde from 3-(4-(2-(4-Hydroxy-3-methoxyphenyl)-2-oxoethoxy) phenyl)acrylaldehyde Pd/C (10 mol %) is weighed into a reaction flask. A solvent mixture consisting of ethyl acetate and water (4:1) and ammonium formate (2 equivalents) is added, the reaction flask is capped with a rubber septa and the mixture is heated (80° C.) for 2 minutes. Substrate 3-(4-(2-(4-hydroxy-3-methoxyphenyl)-2-oxoethoxy)phenyl)-acrylaldehyde is added. The reaction is run for 120 minutes and the reaction is quenched with brine. The product is extracted by DCM and the organic phase is dried by $Na_2SO_4$. The products were purified by silica column to yield the products in above 90% yield.

Example 20

Generating 4-Ethyl-2-methoxyphenol and 4-(3-Hydroxypropyl)phenol from 3-(4-(2-(4-Hydroxy-3-methoxyphenyl)-2-oxoethoxy)phenyl)acrylaldehyde Pd/C (10 mol %) is weighed into a reaction flask. A solvent mixture consisting of ethyl acetate and water (4:1) and ammonium formate (2 equivalents) is added, the reaction flask is capped with a rubber septa and the mixture is heated (80° C.) for 2 minutes. Substrate 3-(4-(2-(4-hydroxy-3-methoxyphenyl)-2-oxoethoxy)phenyl)-acrylaldehyde is added. The reaction is run for 120 minutes and then 3 equivalents of formic acid are added and the reaction is run at 80° C. for 1 hour and the reaction is quenched with brine. The product is extracted by DCM and the organic phase is dried by $Na_2SO_4$. The products were purified by silica column to yield the products in above 90% yield.

Example 21

Generating Ethyl 3-(4-hydroxyphenyl)propanoate and 1-(4-Hydroxy-3-methoxyphenyl)ethanone from Ethyl 3-(4-(2-(4-hydroxy-3-methoxyphenyl)-2-oxoethoxy)phenyl)acrylate Pd/C (10 mol %) is weighed into a reaction flask. A solvent mixture consisting of ethyl acetate and water (4:1) and ammonium formate (2 equivalents) is added, the reaction flask is capped with a rubber septa and the mixture is heated (80° C.) for 2 minutes. Substrate ethyl 3-(4-(2-(4-hydroxy-3-methoxyphenyl)-2-oxoethoxy)phenyl)acrylate is added. The reaction is run for 120 minutes and the reaction is quenched with brine. The product is extracted by DCM and the organic phase is dried by $Na_2SO_4$. The products were purified by silica column to yield the products in above 90% yield.

Example 22

Generating Ethyl 3-(4-hydroxyphenyl)propanoate and and 4-(3-Hydroxypropyl)phenol from Ethyl 3-(4-(2-(4-hydroxy-3-methoxyphenyl)-2-oxoethoxy) phenyl)acrylate Pd/C (10 mol %) is weighed into a reaction flask. A solvent mixture consisting of ethyl acetate and water (4:1) and ammonium formate (2 equivalents) is added, the reaction flask is capped with a rubber septa and the mixture is heated (80° C.) for 2 minutes. Substrate ethyl 3-(4-(2-(4-hydroxy-3-methoxyphenyl)-2-oxoethoxy)phenyl)acrylate is added. The reaction is run for 120 minutes and then 3 equivalents of formic acid are added and the reaction is run at 80° C. for 1 hour and the reaction is quenched with brine. The product is extracted by DCM and the organic phase is dried by $Na_2SO_4$. The products were purified by silica column to yield the products in above 90% yield.

Example 23

Generating Phenol and Ethylbenzene from 2-Phenoxy-1-phenylethanone

Pd/C (10 mol %) is weighed into a reaction flask. A solvent mixture consisting of ethyl acetate and water (4:1) and ammonium formate (2 equivalents) is added, the reaction flask is capped with a rubber septa and the mixture is heated (80° C.) for 2 minutes. Substrate 2-phenoxy-1-phenylethanone is added. The reaction is run for 120 minutes and then 3 equivalents of formic acid is added and the reaction is run at 80° C. for 1 hour and the reaction is quenched with brine. The product is extracted by DCM and the organic phase is dried by $Na_2SO_4$. The products were purified by silica column to yield the products in above 90% yield.

Example 23

Generating 2,3-Bis(benzo[d][1,3]dioxol-5-ylmethyl) butane-1,4-diol from 1,4-Bis(benzo[d][1,3]dioxol-5-yl)hexahydrofuro[3,4-c]furan Pd/C (10 mol %) is weighed into a reaction flask. A solvent mixture consisting of ethyl acetate and water (4:1) and ammonium formate (25 mol %) is added, the reaction flask is capped with a rubber septa and the mixture is heated (80° C.) for 2 minutes. Substrate 1,4-bis(benzo[d][1,3]dioxol-5-yl)hexahydrofuro[3,4-c]furan is added. The reaction is run with 3 equivalents of formic acid for 4 hours and the reaction is quenched with brine. The product is extracted by DCM and the organic phase is dried by $Na_2SO_4$. The products were purified by silica column to yield the products in above 90% yield.

The invention claimed is:

1. A method of reducing a C—O bond to the corresponding C—H bond in a substrate, comprising:
performing a reaction using a hydrogen donor, a metal catalyst and a base in a solvent mixture,
the solvent mixture including at least two solvents, wherein a first solvent of the at least two solvents is water, and
the reaction being conducted at a temperature of at least 40° C.

2. The method according to claim 1, wherein the base is an inorganic base or an organic base.

3. A method of reducing a C—O bond to the corresponding C—H bond in a substrate, comprising:
performing a reaction using a hydrogen donor, a metal catalyst and a base in a solvent mixture,
the solvent mixture including at least two solvents, wherein a first solvent of the at least two solvents is water, and an atmosphere including carbon dioxide, and
the reaction being conducted at a temperature of at least 40° C.

4. The method according to claim 1, wherein the hydrogen donor is formic acid or hydrogen gas.

5. The method according to claim 1, wherein one solvent of the at least two solvents is a polar, unpolar, protic or aprotic solvent.

6. The method according to claim 1, wherein the metal catalyst is a transition metal catalyst.

7. The method according to claim 1, wherein the substrate is an olefin.

8. The method according to claim 1, wherein the substrate is one selected from a benzylic alcohol, allylic alcohol, ester, and ether.

9. The method according to claim 1, wherein the substrate is a polymer or a biopolymer.

10. The method according to claim 1, wherein the hydrogen donor is not hydrogen gas.

11. The method according to claim 1, wherein an amount of the base used is not stoichiometric to an amount of the substrate.

12. The method according to claim 1, wherein an amount of the base is not stoichiometric to an amount of the substrate unless the substrate is an ether either situated in an alpha position to a carbonyl or in a beta position to an alcohol.

13. The method according to claim 1, wherein the reaction is conducted at a temperature of 70-100° C.

14. The method according to claim 1, wherein the metal catalyst is a transition metal catalyst based on palladium.

15. The method according to claim 3, wherein the hydrogen donor is formic acid or hydrogen gas.

16. The method according to claim 9, wherein the polymer or the biopolymer is a lignin.

* * * * *